United States Patent
Lee et al.

(10) Patent No.: US 9,526,678 B2
(45) Date of Patent: Dec. 27, 2016

(54) WATER BASED CREAMY COSMETIC COMPOSITION

(71) Applicant: L'OREAL, Paris (FR)

(72) Inventors: Heather Yoonsoo Lee, Wayne, NJ (US); Angeles Fonolla-Moreno, Scotch Plains, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/565,985

(22) Filed: Dec. 10, 2014

(65) Prior Publication Data
US 2016/0166478 A1 Jun. 16, 2016

(51) Int. Cl.
| | | |
|---|---|---|
| *A61K 8/00* | (2006.01) | |
| *A61K 8/18* | (2006.01) | |
| *A61Q 1/02* | (2006.01) | |
| *A61Q 19/04* | (2006.01) | |
| *A61K 8/06* | (2006.01) | |
| *A61Q 1/10* | (2006.01) | |
| *A61K 8/60* | (2006.01) | |
| *A61K 8/891* | (2006.01) | |
| *A61K 8/37* | (2006.01) | |
| *A61K 8/39* | (2006.01) | |
| *A61K 8/81* | (2006.01) | |

(52) U.S. Cl.
CPC .............. *A61K 8/062* (2013.01); *A61K 8/375* (2013.01); *A61K 8/39* (2013.01); *A61K 8/60* (2013.01); *A61K 8/8147* (2013.01); *A61K 8/8152* (2013.01); *A61K 8/8158* (2013.01); *A61K 8/891* (2013.01); *A61Q 1/10* (2013.01); *A61K 2800/43* (2013.01); *A61K 2800/48* (2013.01); *A61K 2800/594* (2013.01)

(58) Field of Classification Search
None
See application file for complete search history.

(56) References Cited

U.S. PATENT DOCUMENTS

| | | | | |
|---|---|---|---|---|
| 5,658,579 A | * | 8/1997 | LaFleur | A61K 8/25 424/401 |
| 5,763,497 A | * | 6/1998 | Ikeda | A61K 8/06 424/401 |
| 7,879,316 B2 | | 2/2011 | Ferrari et al. | |
| 8,114,389 B2 | | 2/2012 | Douin et al. | |
| 8,865,193 B2 | | 10/2014 | Wolff et al. | |
| 2002/0018791 A1 | | 2/2002 | Vatter et al. | |
| 2002/0086039 A1 | * | 7/2002 | Lee | A61K 8/22 424/401 |
| 2008/0095730 A1 | | 4/2008 | Atis | |
| 2011/0293550 A1 | | 12/2011 | Bui et al. | |
| 2014/0050768 A1 | * | 2/2014 | Struck | C09C 1/0021 424/401 |
| 2014/0086853 A1 | * | 3/2014 | Pham | A61Q 5/12 424/59 |
| 2014/0186282 A1 | | 7/2014 | Patel et al. | |
| 2014/0186411 A1 | * | 7/2014 | Shah | A61K 9/107 424/401 |
| 2014/0227213 A1 | | 8/2014 | Scotland et al. | |

FOREIGN PATENT DOCUMENTS

FR  2792190 A1  10/2000

OTHER PUBLICATIONS

Zimmer et al. (EP1366737A1).*
Kobo Products (Makimousse Eye Shadow with KTZ Aruban 2010).*
Interpolymer Creative Polymer Solutions; Grafted Technology for Cosmetic Applications; Oct. 2013; Interpolymer Corporation, 200 Dan Road, Canton, MA 02021; www.interpolymer.com; info@interpolymer.com.
Interpolymer Creative Poymer Solutions; Technical Information SYNTRAN PC 5288; Feb. 2014; Interpolymer Sarl, 67160 Wissembourg, France; info@interpolymer.fr; www.interpolymer.com.
U.S. Appl. No. 14/985,129, filed Dec. 30, 2015, Motornov, et al.

* cited by examiner

*Primary Examiner* — Robert A Wax
*Assistant Examiner* — Quanglong Truong
(74) *Attorney, Agent, or Firm* — Oblon, McClelland, Maier & Neustadt, L.L.P.

(57) ABSTRACT

Disclosed are low wax, volatile solvent-free eye shadow compositions comprising a, an emulsifying system including a sucrose fatty acid ester and a co-emulsifier, less than 5% of a film forming polymer, viscosity increasing agent, a silicone oil, a filler/powder, water, a pigment and less than 3% wax. Also disclosed are methods for making up and/or enhancing the appearance of eyes by applying said compositions to the eyes and well as methods of making said compositions.

26 Claims, No Drawings

WATER BASED CREAMY COSMETIC COMPOSITION

FIELD OF THE INVENTION

The present invention generally relates to a novel eye shadow composition that is a water-based cream having low amounts of film formers, is easy to remove, and is non-drying to the skin. The invention also relates to methods of making up the eyes with improved removability.

BACKGROUND OF THE INVENTION

Currently available commercial eye shadows are in the form of pressed or loose powders, hot-poured gels, creams, or liquids. The non-powder eye shadows typically contain volatile organic solvents, such as isododecane and a significant amount (greater than about 5%) of film formers, as these components are known to assist in imparting long wear properties to the compositions. Due to the high level of film formers these eye shadows may have a tacky feel. Also, the use of volatile organic solvents makes removal difficult and is drying to the skin.

Additionally, many of the eye shadows on the market result in creasing over time.

There exists a need for long wearing eye shadow that is comfortable, not drying, is crease resistant and is easily removable without use of chemical solvents.

BRIEF SUMMARY OF THE INVENTION

In an embodiment the invention relates to a composition comprising:
  (a) an emulsifying system comprising (i) at least one lipophilic emulsifying surfactant and (ii) at least one sucrose fatty acid ester;
  (b) less than about 5% by weight of at least one film forming polymer selected from an ethylene/acrylic acid copolymer, styrene/acrylates copolymer, and mixtures thereof;
  (c) at least one viscosity increasing agent;
  (d) at least one silicone oil;
  (e) at least one powder, filler, or a mixture thereof;
  (f) water;
  (g) less than about 3% by weight of at least one wax;
  (h) at least one colorant;
  (i) optionally at least one surfactant; and
  (j) optionally at least one slip agent;
  said composition being free of volatile organic solvents; all weights being relative to the total weight of the composition.

Another embodiment of the invention relates to a method of making up and/or enhancing the appearance of eyes by applying to the eyes above cosmetic composition.

Another embodiment of the invention relates to a method of improving at least one property selected from long wear, comfort, crease-resistance, and ease of removal of eye shadow by incorporating in said eye shadow at least one lipophilic emulsifying surfactant and at least one sucrose fatty ester, less than about 5% of at least one forming system comprising at least one polymer selected from an ethylene/acrylic acid copolymer, styrene/acrylates copolymer, and mixtures thereof, at least one viscosity increasing agent, and at least one filler.

Another embodiment of the invention relates to a process for making the above-described cosmetic composition.

The composition optionally may include other components appropriate for its intended use such as preservatives, neutralizers, vitamins, fillers, solvents, anti-wrinkle agents, sun filters, and additional fatty substances, and the like.

DETAILED DESCRIPTION OF THE INVENTION

The current invention provides eye shadow compositions that are comfortable, non-tacky, non-drying, creamy and crease-resistant for prolonged periods of time (are long wearing). This is achieved even without use of volatile organic solvents and/or significant amounts of film formers (e.g. greater than about 5%). These compositions preferably are oil-in-water emulsions. They can be easily removed with just soap and water and do not require use of a makeup remover or excess rubbing.

In the following description of the invention and the claims appended hereto, it is to be understood that the terms used have their ordinary and accustomed meanings in the art, unless otherwise specified. All concentrations are by weight percent on an active basis unless otherwise indicated.

"Aqueous phase" means the phase comprising water as well as such substances of a formulation which, due to their hydrophilic character, can be mixed and/or dissolved and/or dispersed in water. The aqueous phase of the composition according to the invention is advantageously a continuous aqueous phase.

"Easy removal" means the composition may be substantially removed with a non-harsh remover, such as soap and water, and without excessive rubbing.

"Emulsifier or emulsifying surfactant" is a term of art that is well known to those skilled in the art. See, e.g. http://pharmlabs.unc.edu/labs/emulsions/agents.htm. It is a compound that has a hydrophilic part and a lipophilic part ("amphiphilic) and facilitates the dispersion of two mutually insoluble phases, in this case the oil and water phases, assisting in the formation of the O/W emulsion. Such compounds do not have an overall electric charge in their working environment (are "non-ionic").

"Free of," such as free of organic volatile solvents means that the level of these components in the composition is from 0 to about 0.05% by weight, preferably 0%.

"Long wear" compositions as used herein, means the compositions retain at least one property chosen from consistency, texture, and color the same without fading or creasing over extended period of time (typically 6 hours or longer) as viewed by the naked eye. Long wear properties may be evaluated by any method known in the art for evaluating such properties. For example, the consistency, texture and color of the eye shadow composition may be evaluated immediately following application and these characteristics may then be re-evaluated and compared after an individual has worn the eye shadow composition for a certain amount of time.

"Oil phase" or "oily phase" means the phase containing the lipophilic, non-ionic compounds that are liquid at room temperature (25° C.). These compounds include one or more mutually compatible non-aqueous fatty substances that are liquid at room temperature, for example organic solvents and oils ("liquid fatty substances") as herein described, and any lipophilic additive that may be present. The oil phase does not include the charged surfactants.

"Tackiness" as used herein refers to the adhesion between two substances. For example, the more tackiness there is between two substances, the more adhesion there is between the substances. Tackiness can be measured and provided in US 2008/0095730, which, to the extent necessary, is herein incorporated by reference in its entirety.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

In a preferred embodiment, the composition of the invention may be in the form of an oil-in-water emulsion (O/W).

The O/W emulsions according to the invention comprise an oil phase (or lipophilic phase) dispersed in an aqueous phase. In such emulsions, the aqueous phase is thus the continuous phase of the composition while the oil phase is the dispersed phase of the composition. The powders, fillers and/or pigments, and the like, are preferably dispersed in the water phase.

The oil phase is present in an amount ranging from about 5% to about 50%, preferably from about 10% to about 25%, most preferably about 12% to about 20%, including all ranges and subranges therebetween, by weight relative to the total weight of the composition. The aqueous phase is present in an amount ranging from about 50% to about 95%, preferably from about 40% to about 90%, most preferably about 55% to about 80%, including all ranges and subranges therebetween, by weight, relative to the total weight of the composition.

The viscosity of the emulsions, measured at 25° C. with a Rheomat 180 viscometer at 200 rmp (revolutions per minute) using a No. 5 spindle, is preferably greater than or equal to about 20 Pa*s, typically from about 20 to about 45 Pa*s, including all ranges and subranges therebetween. The viscosity varies depending on the color/pigment in the compositions. Viscosity is generally measured 10 minutes after switching on the rotation of the spindle.

The pH of the emulsion of the invention at 25° C. ranges from about 5 to about 6, most preferably about 5.5+/−0.3.

The density of the composition ranges from about 0.7 to about 1.5 g/cm$^3$, most typically about 1.02 g/cm$^3$. Density is measured using a specific gravity cup and weighing it pursuant to standard protocol ASTM D1475.

In one embodiment the invention relates to an eye shadow composition comprising:
 (a) an emulsifying system comprising (i) at least one lipophilic emulsifying surfactant and (ii) one at least one sucrose fatty acid ester;
 (b) less than about 5% by weight of at least one film forming polymer selected from an ethylene/acrylic acid copolymer, styrene/acrylates copolymer, and mixtures thereof;
 (c) at least one viscosity increasing agent;
 (d) at least one silicone oil;
 (e) at least one powder, filler, or a mixture thereof;
 (f) water
 (g) less than about 3% by weight of at least one wax;
 (h) at least one colorant;
 (i) optionally at least one surfactant, nonionic; and
 (j) optionally at least one slip agent;
 said composition being free of volatile organic solvents; all weights being relative to the total weight of the composition.

In another embodiment the invention relates to an eye shadow composition comprising:
 (a) an emulsifying system comprising (i) at least one lipophilic emulsifying surfactant, and (ii) at least one sucrose fatty acid ester;
 (b) less than about 5% by weight of at least one film forming polymer selected from an ethylene/acrylic acid copolymer, styrene/acrylates copolymer, and mixtures thereof;
 (c) at least one viscosity increasing agent;
 (d) at least one silicone oil;
 (e) at least one powder selected from polymeric powders, silicone powders, and mixtures thereof;
 (f) water
 (g) less than about 3% by weight of at least one wax
 (h) at least one colorant;
 (i) at least one surfactant selected anionic surfactant, nonionic surfactant, mixtures thereof; and
 (j) at least one slip agent;
 said composition being free of volatile organic solvents and optionally further comprising at least one or more solvent (s) other than water; all weights being relative to the total weight of the composition.

In another embodiment, the invention relates to a cosmetic composition comprising:
 (a) from about 0.7% to about 7%, by weight, of an emulsifying system comprising (i) from about 0.2% to about 3%, by weight, of at least one lipophilic emulsifying surfactant, and (ii) from about 0.5% to about 4%, by weight, of one at least one sucrose fatty acid ester;
 (b) from about 0.5% to less than about 5%, by weight, of at least one film forming polymer selected from an ethylene/acrylic acid copolymer, styrene/acrylates copolymer, and mixtures thereof;
 (c) from about 0.1% to about 5%, by weight, of at least one viscosity increasing agent;
 (d) from about 2% to about 15%, by weight, of at least one silicone oil;
 (e) from about 1% to about 15%, by weight, of at least one powder selected from polymeric powders, silicone powders, and mixtures thereof;
 (f) from about 20% to about 70%, by weight, of water;
 (g) less than about 3%, by weight, of at least one wax;
 (h) from about 0.5% to about 20%, by weight, of at least one colorant;
 (i) optionally from about 0.1% to about 10%, by weight, of at least one fatty acid ester, sorbitan ester, and mixtures thereof; and
 (j) optionally from about 0.5% to about 20%, by weight, of at least one slip agent;
 said composition being free of volatile organic solvents; said composition optionally further comprising from about 0.1% to about 10%, by weight, of at least one or more solvent other than water; all weights being relative to the total weight of the composition.

In a preferred embodiment, the invention relates to an oil-in-water emulsion comprising:
 (1) an oily phase comprising:
  (a) (i) at least one lipophilic emulsifying surfactant;
  (c) at least one viscosity increasing agent;
  (d) at least one silicone oil:
  (g) less than about 3% by weight of at least one wax; and
  (i) optionally at least one surfactant; and
 (2) an aqueous phase comprising:
  (a) (ii) one at least one sucrose fatty acid ester;
  (b) less than about 5% by weight of at least one film forming polymer selected from an ethylene/acrylic acid copolymer, styrene/acrylates copolymer, and mixtures thereof;
  (e) at least one powder, filler, or a mixture thereof;

(f) water and optionally one or more solvents other than water; and
(h) at least one colorant;
wherein the oily phase is dispersed in the aqueous phase; said emulsion having a viscosity equal to or greater than about 20 Pa*s and being free of volatile organic solvents.

In an embodiment, the composition further comprises at least one slip agent.

In another embodiment, the silicone oil (d) is selected from dimethicone, pentaerythrityl tetraethylhexanoate, cyclohexasiloxane, PEG-10 dimethicone, and mixtures thereof.

In another embodiment, the sucrose fatty acid ester (a)(ii) is sucrose tristearate.

In another embodiment, the at least one viscosity increasing agent (c) is selected from ammonium acryloydimethyltaurate/steraeth-25 methacrylate crosspolymer, sodium polyacrylate and mixtures thereof.

In another embodiment, the film forming polymer (b) is selected from ethylene/acrylic acid copolymer (and) styrene/acrylates copolymer (such as Syntran PC 5288, commercially available from Interpolymer).

The compositions of the invention do not require the use of plasticizers in addition to those that may be included in the raw materials.

Another embodiment of the invention relates to method of improving at least one property chosen from long wear, comfort, crease-resistance, and ease of removal, of an eye shadow cosmetic composition, said method comprising including in the cosmetic composition:
(a) an emulsifying system comprising (i) at least one lipophilic emulsifying surfactant, and (ii) at least one sucrose fatty acid ester;
(b) less than about 5% of at least one film forming polymer selected from an ethylene/acrylic acid copolymer, styrene/acrylates copolymer, and mixtures thereof;
(c) at least one viscosity increasing agent;
(d) at least one silicone oil;
(e) at least one powder, filler, or a mixture thereof;
(f) water; and
(g) less than about 3% of at least one wax.

Emulsifying System (a)

The compositions of the invention include at least one lipophilic emulsifying surfactant (a)(i) and at least one sucrose fatty acid ester (a)(ii). When the invention comprises an O/W emulsion, the lipophilic emulsifying surfactant is present in the oil phase and the sucrose fatty acid ester (a)(ii) is present in the water phase.

Lipophilic Emulsifying Surfactant (a)(i)

A lipophilic emulsifying surfactant is an emulsifying surfactant that is soluble in an oil (thus present in the oil phase).

Examples of such lipophilic emulsifying surfactants include nonionic surfactants, particularly esters of polyols and of fatty acids with a saturated or unsaturated chain containing, for example, from 8 to 24 carbon atoms, preferably from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof; the polyethylene glycol esters of C8-C24 fatty acids, and the oxyalkylenated derivatives thereof; the sorbitol esters of $C_8$-$C_2$4 fatty acids, and the oxyalkylenated derivatives thereof. Glyceryl esters of fatty acids (preferably a stearate) are particularly preferred.

Non-limiting examples of useful glyceryl esters include glyceryl stearate (glyceryl monostearate, distearate and/or tristearate) (CTFA name: glyceryl stearate, such as the product Tegin M Pellets, from Goldschmidt), glycerol stearate citrate, glyceryl ricinoleate, and mixtures thereof.

Polyethylene glycol esters of fatty acids that may be used include polyethylene glycol stearate (polyethylene glycol monostearate, distearate and/or tristearate) and more especially polyethylene glycol 50 OE monostearate (CTFA name: PEG-50 stearate) and polyethylene glycol 100 OE monostearate (CTFA name: PEG-100 stearate), PEG-200 glyceryl stearate, and mixtures thereof.

Mixtures of these surfactants may also be used, for instance the product containing glyceryl stearate and PEG-100 stearate, sold under the name Arlacel 165 by the company Uniqema, and the product containing glyceryl stearate (glyceryl mono-distearate) and potassium stearate, sold under the name Tegin by the company Goldschmidt (CTFA name: glyceryl stearate SE).

In a particular embodiment the lipophilic emulsifying surfactant is glyceryl stearate.

The lipophilic emulsifying surfactant is present in the composition of the invention in an amount of from about 0.2% to about 3%, preferably from about 0.5% to about 1.5%, more preferably from about 0.7% to about 1.2%, including all ranges and subranges therebetween, by weight, all weights being based on the total weight of the composition.

Sucrose Fatty Acid Ester (a)(ii)

Sucrose fatty acid esters are known to be emulsion stabilizers and surfactants. See, e.g., Sucrose Fatty Acid Esters, http://www.cosmeticsinfo.org/ingredient/sucrose-fatty-acid-esters. Non-limiting examples of sucrose fatty acid esters useful in the invention include, for example, sucrose cocoate sucrose laurate (and) aqua (and) alcohol (Surfhope® C-1215 commercially available from Mitsubishi-Kagaku), sucrose laurate, sucrose myristate, sucrose palmitate, sucrose polystearate, sucrose tristearate, sucrose distearate, sucrose stearate, sucrose dilaurate, sucrose hexaerucate, sucrose oleate, sucrose pentaerucate, sucrose polybehenate, sucrose polycottonseedate, sucrose polylaurate, sucrose polylinoleate, sucrose polypalmate, sucrose polyoleate, sucrose polysoyate, sucrose ricinoleate, sucrose tetraisostearate, sucrose tribehenate, sucrose hexaoleate/hexapalmitate/hexastearate, sucrose hexapalmitate, sucrose trilaurate, and mixtures thereof.

Preferred sucrose fatty acid esters include sucrose laurate (and) aqua (and) alcohol, sucrose laurate, sucrose myristate, sucrose palmitate, sucrose polystearate, sucrose tristearate, sucrose distearate, sucrose stearate, and mixtures thereof, all of which are commercially available from Mitsubishi-Kagaku under the tradename Surfhope® C. The sucrose fatty acid ester may be used, for example, as a mixture with other ingredients, for example alcohol, such as the products sold, for example, by Mitsubishi-Kagaku under the trade name Surfhope® C. Alternatively the sucrose fatty acid may also be used without additives, for example, such as the product Ryoto Sugar Ester S 370 (Ryoto). Particularly preferred sucrose fatty acid esters include sucrose stearate, sucrose distearate, sucrose tristearate, and mixtures thereof, and most particularly sucrose tristearate.

The sucrose fatty acid ester is present in the composition of the invention in an amount of from about 0.5% to about 4%, preferably from about 1% to about 3%, more preferably about 1.2% to about 1.7%, including all ranges and subranges therebetween, by weight, all weights being based on the total weight of the composition.

Film Former (b

The compositions of the invention include at least one film forming polymer selected from ethylene/acrylic acid copolymer, styrene/acrylates copolymer, and mixtures thereof.

As used herein, the terms "film-forming polymer," "film former," "film-forming agent" and variations thereof mean a polymer capable of, by itself or in the presence of an auxiliary film-forming agent, forming a continuous film that adheres to a support and especially to keratin materials, for instance the eye lids.

In an embodiment the film former (b) is a polyacrylate latex film former selected from an olefin grafted polymer and a styrene acrylate copolymer. Examples of such polymers as well as methods of making such olefin grafted polymers are described in U.S. Pat. No. 8,865,193, herein incorporated by reference. In a particular embodiment, the olefin grafted polymer is selected from ethylene/acrylic acid copolymer (and) styrene/acrylates copolymer (SYNTRAN® PC5288), olefin/acrylate grafted polymer (and) sodium laureth sulfate (and) C12-15 SEC-pareth 15 (commercially available as SYNTRAN® EX108), acrylates copolymer (and) butylene glycol (and) sodium laureth sulfate (SYNTRAN® EX53), olefin/acrylic graft emulsion (SYNTRAN® EX142 and SYNTRAN® 108GC). The Syntran polymers are commercially available from Interpolymer.

In a preferred embodiment the film former (b) is ethylene/acrylic acid copolymer (and) styrene/acrylates copolymer, a commercial example of which is SYNTRAN® PC5288 from Interpolymer.

In accordance with various exemplary embodiments, the at least one film former may be present in the cosmetic composition in an amount, or a combined amount when more than one film former is used, ranging from about 0.5% to about 5%, typically from about 0.6% to about 3%, more typically from about 1% to about 2.5%, more typically from about 1.3% to about 2%, including all ranges and subranges therebetween, by weight (non-dry weight basis), relative to the total weight of the compositions.

Viscosity Increasing Agent ("Thickener" or "Rheology Increasing Agent") (c)

Representative viscosity increasing agents include thickening agents and gelling agents. The viscosity increasing agent(s) that may be useful in the practice of embodiments of the disclosure include those conventionally used in cosmetics such as polymers of natural origin and synthetic polymers.

Viscosity increasing agents may be selected from, for example vegetable gums, liposoluble/lipodispersible polymers, salts, and mixtures thereof.

Representative viscosity increasing agents that may be used in the practice of embodiments according to the disclosure may be chosen from nonionic, anionic, cationic, and amphoteric polymers, including acrylate-based polymers, polysaccharides, polyamino compounds, amphiphilic polymers, and other viscosity modifiers such as cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives (e.g., hydroxypropyl guar, cationic guar derivatives, etc.), gums such as gums of microbial origin (e.g., xanthan gum, scleroglucan gum, etc.), and gums derived from plant exudates (e.g., gum arabic, ghatti gum, karaya gum, gum tragacanth, carrageenan gum, agar gum and carob gum), pectins, alginates, and starches, crosslinked homopolymers of acrylic acid or of acrylamidopropane-sulfonic acid, associative polymers, non-associative thickening polymers, water-soluble thickening polymers, and mixtures of these.

Other non-limiting examples of such agents include, glycerol behenate, polyethylene and copolymers thereof such as PEG-150 distearate, magnesium stearate, synthetic polymers such as polyacrylic acid (available commercially as Carbomers) and acrylates copolymers such as sodium polyacrylate and polyacryloyldimehtyl taurate, and mixtures of these.

In an embodiment, the viscosity increasing agent is selected from ammonium polyacryloyldimethyl taurate, ammonium acryloydimethyltaurate/steraeth-25 methacrylate crosspolymer, sodium polyacrylate, sorbitol/sebacic acid copolymer behenate, ethylenedaimines/stearyl dimer dilinoleate copolymer, and mixtures thereof.

In a particular embodiment, the viscosity increasing agent is selected from ammonium acryloydimethyltaurate/steraeth-25 methacrylate crosspolymer (such as Aristoflex HMS, commercially available from Clariant), sodium polyacrylate (such as Cosmedia from Cognis/BASF), and mixtures thereof.

The viscosity increasing agent is present in the composition of the invention in an amount of from about 0.1% to about 5%, preferably from about 0.2% to about 3.0%, more particularly from about 0.5% to about 2.5%, by weight, including all ranges and subranges therebetween, by weight, including all ranges and subranges therebetween, all weights being based on the total weight of the composition.

Silicone Oil and Other Liquid Fatty Substances (d)

The compositions of the invention include at least one silicone oil or silicone oil derivative. The term "silicone oil" means an oil containing at least one silicon atom, and especially containing Si—O groups.

Volatile and non-volatile silicone oils, may be used. Such oils are described, for example in US 2011/0293550, which to the extent required, is herein incorporated by reference. Suitable silicone oils include, for instance, volatile or non-volatile polymethylsiloxanes (PDMS) with a linear or cyclic silicone chain, which are liquid or pasty at room temperature, including cyclopolydimethylsiloxanes (cyclomethicones) such as cyclohexasiloxane; polydimethyl-siloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenyl-siloxanes, diphenyl dimethicones, diphenylmethyl-diphenyltrisiloxanes or 2-phenylethyl trimethylsiloxy silicates, and polymethylphenylsiloxanes (trimethyl pentaphenyl trisiloxane); dimethicone; amodimethicone; PEG-10 dimethicone; dimethiconol; cyclemethicone, phenyltrimethicone; aminopropyl phenyltrimethicone; cetyl dimethicone; alkyl dimethicone; potassium dimethicone PEG-7 pantheyl phosphate; and mixtures thereof.

A non-limiting example of a silicone oil derivative is pentaerythrityl tetraethylhexanoate, (for example Trivent PE, available form Alzo).

The compositions optionally may also include a non-volatile, non-silicone liquid fatty substances. Exemplary useful organic non-silicone, non-volatile oils/solvents include polyalphaolefins such as hydrogenated polydecene, hydrogenated polyisobutene, hydrogenated C6-14 olefin polymers and polydecene.

Natural oils may also be used so long as they are physiologically acceptable. Such oils include hydrocarbon-based plant oils with a high triglyceride content such as sweet almond oil, avocado oil, olive oil, candlenut oil, vitamin E oil, and the like. In an embodiment the silicone and/or its derivative oil is selected from dimethicone, PEG-10 dimethicone, pentaerythrityl tetraethylhexanoate, cyclohexasiloxane, and mixtures thereof.

The silicone oil and or silicone oil derivative is present in the composition of the invention in an amount of from about 2% to about 15%, preferably from about 3% to about 10%, more particularly from about 5% to about 9%, by weight, including all ranges and subranges therebetween, all weights being based on the total weight of the composition.

If present, the non-silicone liquid fatty substances can be present in an amount ranging from about 1% to about 6%, typically from about 2% to about 5%, by weight, including all ranges and subranges therebetween, all weights being based on the total weight of the composition.

Powders/Fillers (e)

The compositions of the invention include at least one powder, filler, or mixtures thereof (herein collectively referred to as "fillers") commonly used in the art in cosmetic compositions.

The fillers may be lamellar or non-lamellar, inorganic or organic particles. Representative, non-limiting examples of these ingredients include mica, silica, kaolin, iron oxides, titanium dioxide, polyamide powders, poly-alanine powders, polyethylene powders, tetrafluoroethylene polymer powders, for instance polytetrafluoroethylene(Teflon®), lauroyllysine, silicon powders, starch, boron nitride, polymeric powders, polymethyl methacrylate particles and silicone resin microbeads (for example, Tospearls® from Toshiba), precipitated calcium carbonate, perlite, magnesium carbonate, magnesium hydrocarbonate, hydroxyapatite, hollow silica microspheres (Silica Beads® from Maprecos), glass or ceramic microcapsules.

In an embodiment, the compositions include at least one polymeric powder, silicon powder, and mixtures thereof.

Useful polymeric fillers can include, for example, lamellar or nonlamellar, colorless or white polymeric particles. In certain embodiments, the polymeric filler may be chosen from polyamide powders, such as Nylon® or Orgasol® powders from Arkema; cellulose poly-β-alanine and polyethylene powders; tetrafluoroethylene polymer powders, such as Teflon® powders; lauroyllysine; polymeric hollow microspheres such as those of polyvinylidene chloride/acrylonitrile, for instance Expancel® from Nobel Industries; acrylic powders such as acrylonitrile/methyl methacrylate/vinylidene chloride copolymer (Expancel 551, Akzo Nobel), and Polytrap® powders from Dow Corning; silicone resin microbeads, such as Tospearls® from Toshiba; elastomeric polyorganosiloxane particles, such as those obtained by polymerization of organopolysiloxane having at least two hydrogen atoms each bonded to a silicon atom and of an organopolysiloxane comprising at least two ethylenically unsaturated groups, for instance, two vinyl groups, in the presence of a platinum catalyst; and metal soaps derived from organic carboxylic acids comprising from 8 to 22 carbon atoms, such as from 12 to 18 carbon atoms, for example, zinc stearate, magnesium stearate, lithium stearate, zinc laurate, and magnesium myristate.

Silicone elastomer powders are also useful polymeric fillers. These powders include, but are not limited to, diphenyl dimethicone/vinyl diphenyl dimethicone/silsesquioxane crosspolymer (e.g. KSP 300 from Shin Etsu), vinyl dimethicone/methicone silsesquioxane crosspolymer (e.g KSP 100, Shin Etsu), methylsilanol/silicate crosspolymer, and the powders sold under the names Trefil® Powder E-505C and Trefil® Powder E-506C by Dow Corning.

Acrylic polymer powders may also be used as fillers. Such powders include methacrylate polymers, for example methyl methacrylate/glycol dimethacrylate crosspolymer, methyl methacrylate crosspolymer, polymethyl methacrylate powders, polymethyl methacrylate/ethylene glycol dimethacrylate powders, polyallyl methacrylate/ethylene glycol dimethacrylate powders, and ethylene glycol dimethacrylate/lauryl methacrylate copolymer powders, and mixtures thereof.

Commercial examples of acrylic polymer powder products include methacrylate polymers such as polymethyl methacrylate powders sold under the name Covabead® LH85 by Wacker, DSPCS-12 series and SPCAT-12 from Kobo, and Poly-Pore 200 series from Amcol, and Techpolymer MBP-8 (methyl methacrylated crosspolymer), from Sekisui Plastics; the polymethyl methacrylate/ethylene glycol dimethacrylate powders sold under the names Microsponge® 5640 Skin Oil Adsorber (methyl methacrylate/glycol dimethacrylate crosspolymer; by Dow Corning) and Ganzpearl® GMP-0820 by Ganz Chemical; the polyallyl methacrylate/ethylene glycol dimethacrylate powders sold under the name Poly-Pore® L200 and Poly-Pore® E200 by Amcol; and acrylic acid copolymers available from Dow Corning/Enhanced Derm Technologies under the name Polytrap® (for example ethylene glycol dimethacrylate/lauryl methacrylate copolymer powder, sold under the name Polytrap® 6603).

Examples of suitable acrylic polymer powders are provide in US2002/018791, and US 2014/227213.

In a particular embodiment powder is selected from diphenyl dimethicone/vinyl diphenyl dimethicone/silsesquioxane crosspolymer (e.g. KSP 300 from Shin Etsu), vinyl dimethicone/methicone silsesquioxane crosspolymer, acrylonitrile/methyl methacrylate/vinylidene chloride copolymer, and mixtures thereof. In an embodiment the compositions further include perlite.

The fillers/powders are present in the compositions of the invention in an amount of from about 1% to about 15%, preferably from about 2% to about 12%, more particularly from about 5% to about 10%, by weight, including all ranges and subranges therebetween.

Water (f) and Water Miscible Solvents

The compositions for the invention also comprise water, preferably in an amount ranging from about 20% to about 70%, preferably from about 35% to about 65%, most typically from about 45% about 55%, including all ranges and subranges therebetween, by weight, relative to the total weight of the compositions.

The compositions of the invention may include additional solvents. In particular, the aqueous phase may include at least one solvent that is water-miscible and is not an organic volatile solvent. Non-limiting examples of suitable water-miscible solvents include $C_{1-4}$ alkanols, such as ethanol and isopropanol; glycerol; glycols and glycol ethers such as 2-butoxyethanol, propylene glycol, butylene glycol, monomethyl ether of propylene glycol, monethyl ether and monomethyl ether of diethylene glycol, aromatic alcohols such as benzyl alcohol and phenoxyethanol; analogous products and mixtures of the foregoing products.

Other solvents include caprylic/capric acid triglycerides (such as those sold under the trade name Miglyol®.

In addition to water, the compositions of the invention may comprise a water-miscible solvent in an amount ranging from about 0.1% to about 10%, preferably from about 3% to about 7%, including all ranges and subranges therebetween, by weight, relative to the total weight of the compositions.

Waxes (g)

The cosmetic compositions disclosed herein further comprise less than about 3% of at least one wax. A "wax" as defined herein is a generally lipophilic compound that is solid at room temperature (25° C.), with a solid/liquid reversible change of state, having a melting point of greater than or equal to 30° C., which may be up to 120° C.

By bringing the wax into a liquid state (melting), it is possible to make it miscible with oils and to form a microscopically uniform mixture, but on cooling the mixture to room temperature, recrystallization of the wax in the oils of the mixture is obtained. For example, the waxes that may be used herein may have a melting point of greater than 45° C., such as greater than or equal to 50° C., or greater than or equal to 55° C. The melting point of the wax may be measured using known methods in the art, for instance, by using a differential scanning calorimeter (DSC)

The waxes that may be used in the cosmetic compositions disclosed herein are chosen from waxes that are solid and rigid at room temperature, of animal, plant, mineral or synthetic origin, and mixtures thereof.

Non-limiting examples of waxes that may be used in compositions of the instant disclosure include hydrocarbon-based waxes such as beeswax, lanolin wax and Chinese insect waxes; rice wax, carnauba wax, candelilla wax, ouricury wax, esparto grass wax, cork fibre wax, sugar cane wax, Japan wax and sumach wax; montan wax, microcrystalline waxes, paraffins and ozokerite; polyethylene waxes, the waxes obtained by Fisher-Tropsch synthesis and waxy copolymers, and esters thereof. Silicone waxes and fluoro waxes may also be used.

Waxes obtained by catalytic hydrogenation of animal or plant oils comprising linear or branched $C_8$-$C_{32}$ fatty chains are also suitable for use in the compositions of the disclosure. Among these oils, mention may be made, for example, of hydrogenated jojoba oil, isomerized jojoba oil such as the trans-isomerized partially hydrogenated jojoba oil manufactured or sold by the company Desert Whale under the trade name "Iso-Jojoba-50®", hydrogenated sunflower oil, hydrogenated castor oil, hydrogenated coconut oil and hydrogenated lanolin oil, bis(1,1,1-trimethylolpropane) tetrastearate sold under the name "Hest 2T-4S" by the company Heterene, and bis(1,1,1-trimethylolpropa-ne) tetrabehenate sold under the name "Hest 2T-4B" by the company Heterene.

Further non-limiting examples of suitable waxes include the wax obtained by hydrogenation of olive oil esterified with stearyl alcohol, sold under the name "Phytowax Olive 18 L 57", or the waxes obtained by hydrogenation of castor oil esterified with cetyl alcohol, sold under the name "Phytowax Ricin 16L64 and 22L73" by the company Sophim, may also be used. Such waxes are described in French Patent Application No. 2 792 190, incorporated herein by reference in its entirety.

Preferably, the wax is "non-tacky," meaning, a wax with a tack of less than 0.7 N.s. See, e.g, US Pub. 2014/0186282

In a particular embodiment, the wax is selected from beeswax.

The wax is present in the compositions of the invention in an amount less than about 3%, in particular from about 0.1% to about 2.8%, more particularly from about 0.3% to about 2%, even more particularly from about 0.5% to about 1.5%, by weight, including all ranges and subranges therebetween.

Colorant (h)

As disclosed herein, the cosmetic composition comprises at least one dyestuff, pigment or colorant (herein jointly referred to a "colorant"). Suitable colorants include but are not limited to pulverulent dyestuffs, liposoluble dyes, and water-soluble dyes.

The pulverulent dyestuffs may, for instance, be chosen from pigments and nacres.

The pigments, which may be used according to the present disclosure, may, in certain embodiments, be chosen from white, colored, inorganic, organic, polymeric, non-polymeric, coated and uncoated pigments. Representative examples of inorganic pigments include titanium dioxide, optionally surface-treated, zirconium oxide, zinc oxide, cerium oxide, iron oxide, chromium oxide, manganese violet, ultramarine blue, chromium hydrate, and ferric blue. Non-limiting examples of organic pigments include carbon black, pigments of D&C type, and lakes based on cochineal carmine, barium, strontium, calcium, and aluminum.

The nacres which may be used according to the present invention may be chosen, for example, from white nacreous pigments such as mica coated with titanium or with bismuth oxychloride, colored nacreous pigments such as titanium mica with iron oxides, titanium mica with iron oxides, titanium mica with ferric blue or chromium oxide, titanium mica with an organic pigment chosen from those mentioned above, and nacreous pigments based on bismuth oxychloride.

Representative liposoluble dyes which may be used according to the present disclosure include Sudan Red, DC Red 17, DC Green 6, β-carotene, soybean oil, Sudan Brown, DC Yellow 11, DC Violet 2, DC Orange 5, annatto, and quinoline yellow.

The water-soluble dyes which may be used according to the present invention include, but are not limited to, beetroot juice, methylene blue, the disodium salt of ponceau, the disodium salt of alizarin green, quinoline yellow, the trisodium salt of amaranth, the disodium salt of tartrazine, the monosodium salt of rhodamine, the disodium salt of fuchsin, and xanthophyll.

The at least one colorant is typically present in the cosmetic composition in an amount ranging from about 0.5% to about 20%, typically from about 2% to about 17%, more typically from about 5% to about 12% by weight of the total weight of the composition, including all ranges and subranges therebetween.

Surfactants (Optional) (i)

The cosmetic composition according to the disclosure optionally may further comprise at least one surfactant. In certain embodiments the surfactant is selected from at least one anionic surfactant, nonionic surfactant, and mixtures thereof.

Non-limiting examples of suitable anionic surfactants may include, but are not limited to, fatty acids such as $C_{16}$-$C_{24}$ fatty acids and combinations thereof. As used herein, the term "fatty acid" means a carboxylic acid with a long aliphatic carbon chain. The fatty acid may be chosen from any saturated or unsaturated, linear or branched fatty acids, for instance, palmitic acid, margaric acid, stearic acid, nonadecylic acid, arachidic acid, heneicosylic acid, behenic acid, tricosylic acid, lignoceric acid, and mixtures thereof.

Other suitable anionic surfactants include, by way of non-limiting example:
- polyoxyethylenated fatty acid salts, for example, those derived from amines or alkali metal salts, and mixtures thereof;
- phosphoric esters and salts thereof, such as "DEA oleth-10 phosphate" ("Crodafos N 10N" from the company Croda);

sulfosuccinates such as "Disodium PEG-5 citrate lauryl sulfosuccinate" and "Disodium ricinoleamido MEA sulfosuccinte";

alkyl ether sulfates, such as sodium lauryl ether sulfate; isethionates;

acylglutamate such as "Disodium hydrogenated tallow glutamate" ("Amisoft HS-21 R" sold by the company Ajinomoto);

2-amino-2-methyl-1,3-propanediol (AMPD); and mixtures thereof.

The anionic surfactant may be present in the cosmetic composition in an amount ranging from about 0.01% to about 10% by weight, for instance, from about 0.1% to about 5% by weight, particularly from about 0.3 to about 3% by weight, more particularly 0.5% to about 1% by weight, relative to the total weight of the cosmetic composition, including all ranges and subranges therebetween.

Non-limiting examples of suitable nonionic surfactants may include, but are not limited to, saccharide esters and ethers such as sorbitan esters. Sorbitan esters of $C_{16}$-$C_{22}$ saturated, unsaturated and branched chain fatty acids are particularly useful. Because of the manner in which they are typically manufactured, these sorbitan esters usually comprise mixtures of mono-, di-, tri-, etc., esters. Representative examples of suitable sorbitan esters include sorbitan monooleate (e.g., SPAN® 80), sorbitan sesquioleate (e.g., Arlacel® 83 from Uniqema, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present disclosure.

Other suitable sucrose esters and ethers include sucrose stearate, sucrose cocoate, methylglucose isostearate, sucrose (poly)palmitostearate, sucrose laurate, sucrose palmitate, sucrose tribehenate, sucrose oleate, sucrose distearate, sucrose polylaurate, sucrose laurate and sucrose hexaerucate, and mixtures thereof, for example Arlatone 2121® sold by the company ICI or Span 65V from the company Uniqema.

The nonionic surfactant may be present in the cosmetic composition in an amount ranging from about 0.01% to about 10% by weight, for instance, from about 0.1% to about 5% by weight, particularly from about 0.3 to about 3% by weight, more particularly from about 0.5 to about 2.5% by weight, relative to the total weight of the cosmetic composition, including all ranges and subranges therebetween.

The total amount of surfactant(s) present in the cosmetic composition typically ranges from about 0.01% to about 10% by weight, for instance, from about 0.1% to about 7% by weight, particularly from about 0.3 to about 5% by weight, more particularly from about 0.5% to about 3% by weight, relative to the total weight of the cosmetic composition, including all ranges and subranges therebetween.

Slip Agents/Silicone Elastomer Blends (Optional)(j

The cosmetic compositions optionally may comprise at least one slip agent. Slip agents help other components of a cosmetic formula spread over the skin. Often, these agents also have humectant properties.

Non-limiting examples of slip agents include propylene glycol, butylene glycol, polysorbates, and glycerin.

Silicone elastomer blends may also function as slip agents. Silicone elastomer blends useful according to various embodiments of the disclosure may comprise at least one silicone cross-polymer chosen, for example, from dimethicone/vinyl dimethicone cross-polymers and dimethicone/phenyl vinyl dimethicone cross-polymers. In other embodiments, the silicone cross-polymer may be modified by one or more groups chosen from alkyl, polyether, polyglycerin groups. For instance, the alkyl modified silicone cross-polymers may be chosen from vinyl dimethicone/lauryl dimethicone cross-polymers, cetearyl dimethicone cross-polymers, and $C_{30}$-$C_{45}$ alkyl cetearyl dimethicone cross-polymers. Non-limiting examples of polyether modified silicone cross-polymers include dimethicone/PEG-10/15 cross-polymers. Suitable alkyl and polyether modified silicone cross-polymers may be chosen, for example, from PEG-10/lauryl dimethicone cross-polymers and PEG-15/lauryl dimethicone cross-polymers. Exemplary polyglycerin modified silicone cross-polymers include dimethicone/polyglycerin-3 cross-polymers and lauryl dimethicone/polyglycerin-3 cross-polymers.

The silicone cross-polymer may be dispersed in at least one oil. In certain embodiments, the oil may be chosen from silicone oils, such as cyclic and linear organopolysiloxanes. Cyclic organopolysiloxanes may include, for example, cyclotetrasiloxane; cyclopentasiloxane; and methylated cyclic organopolysiloxanes, e.g., octamethylcyclotetrasiloxane and decamethylcyclopentasiloxane. Non-limiting examples of linear organopolysiloxanes include low molecular weight dimethicones; high molecular weight dimethicones; alkyl derivatives of linear organopolysiloxanes, e.g., cetyl dimethicone and lauryl trimethicone; aryl derivatives of linear organopolysiloxanes, e.g., phenyl trimethicone; and hydroxylated derivatives of linear organopolysiloxanes, e.g., dimethiconol. In other embodiments, the oil may be chosen from organic oils, such as mineral oil; linear and branched alkanes, e.g., isododecane; triethylhexanoin; and squalane.

In an embodiment, the slip agent optionally may be selected from a dimethicone/vinyl dimethicone cross-polymer such as KSG 16 (dimethicone (and) dimethicone/vinyl demthiconecrosspolymer), commercially available from Shin Etsu.

If present in the composition, these additives may constitute from about 0.5% to about 20%, typically from about 2% to about 15%, more particularly about 3% to about 10%, including all ranges and subranges therebetween, by weight relative to the total weight of the composition.

Further Optional Additives

The compositions of the present invention can also include any additional ingredient or additive usually used in the field of eye shadow compositions.

For example, these may be chosen from, for example, solvents, dispersants, antioxidants (such as pentaerythrityl tetra-di-t-butyl hydroxyhydrocinnamate), preservatives (such as phenoxyethanol, sodium benzoate), fragrances, additional thickeners or texturizers, additional liquid lipids/oils, additional viscosity modifiers, additional film formers, sunscreen agents, additional pigments/colorants/dyes, silica, clays, humectants/emollients and moisturizing agents, additional emulsifying agents, structuring agents and additional fillers, additional surfactants, shine agents, conditioning agents, cosmetically, dermatologically and pharmaceutically active agents, vitamins, plant extracts, pH modifiers/neutralizing agents, stabilizers, and mixtures thereof. A non-exhaustive listing of such ingredients is found in U.S. Pat. No. 7,879,316, the entire content of which is hereby incorporated by reference. Additional examples of additives may be found in the *International Cosmetic Ingredient Dictionary and Handbook* ($9^{th}$ ed. 2002, and subsequent editions).

One of skill in the art will be able to select appropriate types and amounts of additional cosmetic ingredients, based on, for example, the type of cosmetic composition being formulated and the desired properties thereof. Any one or more of the additional components set forth above may be included in the compositions.

If present in the composition, these additives may constitute from 2% to 30%, typically from about 5% to about 15%, and more typically from about 6% to about 10%, including all ranges and subranges therebetween, by weight relative to the total weight of the composition.

Cosmetic Methods

In an embodiment according to the invention, the compositions comprising an emulsifying system including at least one lipophilic emulsifying surfactant and at least one sucrose fatty acid ester, less than about 5% of a film forming system, at least one viscosity increasing agent, at least one silicone oil, water, at least one filler and/or powder, and at least one wax afford an eye shadow composition that is long-wearing, crease-resistant, comfortable and ease to remove. Accordingly, another embodiment of the invention provides a method of making up/or enhancing the appearance of eyes by applying to the eyes topically the composition of the present invention in a sufficient amount to make up the eyes. The compositions may be applied to the eyes as needed, preferably once or twice daily.

The compositions according to various exemplary embodiments of the invention may also have improved and/or increased ease of removability. In various embodiments, ease of removability relates to ease of removing the composition from the eyes with warm (e.g. about 50° C. or higher) water. Optionally, conventional cleansing agents such as soap or make-up remover may also be used. As such, the disclosure also relates to methods of improving or increasing the ease of removability of eye shadow compositions by incorporating into said eye shadow compositions at least one hydrophilic emulsifying surfactant, at least one sucrose fatty acid ester, less than about 5% of a film forming system, and a viscosity increasing agent as described herein.

The cosmetic composition according to the invention may be packed in a cosmetic container delimiting at least one compartment which comprises the cosmetic composition, the container being closed by a closing member.

The container may be, according to various embodiments, combined with an applicator, such as a brush or sponge applicator.

The container may be at least partially made of thermoplastic material. Examples of thermoplastic materials that may be mentioned include polypropylene or polyethylene. Alternatively, the container may be made of non-thermoplastic material, such as glass or metal (or alloy).

Process for Making

In an embodiment the invention is directed to a process of making a cosmetic composition comprising:
(a) providing an emulsifying system comprising (i) at least one lipophilic emulsifying surfactant, and (ii) at one at least one sucrose fatty acid ester;
(b) providing at least one film forming polymer selected from an ethylene/acrylic acid copolymer, styrene/acrylates copolymer, and mixtures thereof;
(c) providing at least one viscosity increasing agent;
(d) providing at least one silicone oil
(e) providing at least one powder, filler, or a mixture thereof;
(f) providing water
(g) providing at least one wax;
(h) providing at least one colorant;
(i) optionally providing at least one surfactant; and
(j) optionally providing at least one slip agent;
and combining the above components such as to provide a uniform, blended composition.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the invention. Other embodiments will be apparent to those skilled in the art from consideration of the disclosure and practice of the various exemplary embodiments disclosed herein.

Unless otherwise indicated, all numbers used in the specification and claims are to be understood as being modified in all instances by the term "about," whether or not so stated. It should also be understood that the precise numerical values used in the specification, including the examples and claims, form additional embodiments of the invention, and are intended to include any ranges which can be narrowed to any to end points disclosed within the exemplary ranges and values provided. Efforts have been made to ensure the accuracy of the numerical values disclosed. However, any measured value can inherently contain certain errors resulting from the standard deviation found in its respective measuring technique.

EXAMPLES

The following Examples are intended to be non-restrictive and explanatory only, with the scope of the invention being defined by the claims.

Method of Preparation:

The eye shadow compositions described below were prepared by mixing, independently, the components set forth in Table 1 below, as follows:

1) An oil in water emulsion was prepared by mixing the water phase (water, sucrose fatty acid ester and optional solvents) and oil phase (lipophilic emulsifier, thickener, silicone oil, wax and surfactants) at around 70° C. with the mixing speed of 1200-1300 rpm (the glycerin was added with the water phase);
2) To the O/W emulsion of 1) the film former was added at a temperature of about 50° C. with mixing;
3) To the composition in 2) above the fillers and thickeners were added at room temperature with mixing;
4) To 3) above the pigments/pearls were added with mixing; and
5) Dimethicone crosspolymer was added to 4) and the composition was mixed until uniform.

TABLE 1

Examples 1-2

| Function | INCI US | Ex. 1 (wt % actives) | Ex 2 (wt % actives) |
|---|---|---|---|
| wax (g) | beeswax | 1 | 1 |
| Silicone oil/ derivative (d) | pentaerythrityl tetraethylhexanoate | 2 | 2 |
| filler (e) | perlite | 1 | 1 |
| colorant (h) | mica (and) iron oxides (and) | 7 | |

TABLE 1-continued

Examples 1-2

| Function | INCI US | Ex. 1 (wt % actives) | Ex 2 (wt % actives) |
|---|---|---|---|
| | iron oxides (and) titanium dioxide | | |
| colorant (h) | mica (and) titanium dioxide | 3 | 3 |
| colorant (h) | mica (and) titanium dioxide (and) iron oxides | | 3 |
| Colorant (h) | mica (and) iron oxides | | 4 |
| Liquid fatty substance (optional) | hydrogenated polyisobutene | 4.3 | 4.3 |
| thickener (c) | sodium polyacrylate | 0.45 | 0.45 |
| thickener (c) | ammonium acryloyldimethyltaurate/ steareth-25 methacrylate crosspolymer | 0.5 | 0.5 |
| film former (b) | ethylene/acrylic acid copolymer (and) styrene/ acrylates copolymer | 1.56 | 1.56 |
| powder (e) | acrylonitrile/methyl methacrylate/vinylidene chloride copolymer | 0.18 | 0.18 |
| silicone oil (d) | dimethicone | 2 | 2 |
| silicone oil (d) | cyclohexasiloxane | 3 | 3 |
| slip agent (j) | dimethicone (and) dimethicone/vinyl dimethicone crosspolymer | 1.52 + 0.48 = 2 | 1.52 + 0.48 = 2 |
| powder (e) | vinyl dimethicone/methicone silsesquioxane crosspolymer | 3 | 3 |
| silicone oil (d) | peg-10 dimethicone | 1 | 1 |
| powder (e) | diphenyl dimethicone/vinyl diphenyl dimethicone/ silsesquioxane crosspolymer | 3 | 3 |
| | alcohol denat. | 3 | 3 |
| | water | about 51 | about 51 |
| slip agent (j) | glycerin | 5 | 5 |
| nonionic surfactant (i) | sorbitan sesquioleate | 1 | 1 |
| anionic surfactant (i) | stearic acid | 0.80 | 0.80 |
| emulsifier (a)(i) | glyceryl stearate | 1 | 1 |
| emulsifier (a)(ii) | sucrose tristearate | 1.5 | 1.5 |
| optional additives (preservatives, solvents, and the like) | | QS | QS |

Comparative Testing

In vivo wear test:

Protocol:

17 women participated in the study. No products were used on the eye area on the morning of study. Upon arrival, they cleansed their eye area with L'Oreal Oil Free Eye Makeup Remover and makeup removing cotton pads. The skin was permitted to air dry for five (5) minutes prior to capturing baseline images. All images were acquired with closed eyes, using the Canfield Photography System.

Panelists were subsequently instructed to apply the shadow on both of their upper eyelids, such that the area was completely covered up to the crease. After a 1 minute drying time, a post application image was acquired. Subjects were released and instructed (with instruction sheet) to return at 7 hours post-application for images.

An independent evaluator rated the photographs using a four-(4) point rating scale, where 0=no color, 1=slight color, 2=moderate color, and 3=looks like initial application. For a product to be considered to "wear" at a designated number of hours after application, the median score should be two (2) or higher, according to the grading criteria, for that designated time period.

Results:

The composition of Example 1 was found to wear at seven (7) hours after application and was crease-resistant 7 hours after product application.

Swab and Flake tests/in-vitro (show wear and non-dryness)

Protocol:

A 0.2 g of the composition of Ex. 1 was rubbed onto Bioskin. A swab was clipped onto a mixer set to 30 rpm. The mixer was run for 2 min with the swab rubbing the sample on the Bioskin. Evaluation of the Bioskin sample was made with the naked eye at T0 min.

The sample was then placed in a 37° C. chamber for 20 min. The test was run again with the swab rubbing the sample and the Bioskin sample was evaluated with naked eye at T20 min.

The sample was then placed in a 37° C. chamber for 180 min, the swab rub test repeated, and Bioskin sample evaluated again.

Wear was evaluated by assessing how much sample remains on the Bioskin.

The scale was: 0=bad wear, 1=moderate wear, 2=very good wear.

Flaking was evaluated by assessing how much of the sample flaked off at T20 (after drying in 37° C. chamber for 20 min) and at T180 (after drying in 37° C. chamber for 180 min).

The scale was: 0=no flakes, 1=flakes.

The results of this test are summarized in Table 2 below.

TABLE 2

Wear/Flake Test

| Composition | Wear rating at T0 | Wear rating at T20 | Wear rating at T180 | Flake rating at T20 | Flake rating at T180 |
|---|---|---|---|---|---|
| Ex 1 | 1 | 1 | 2 | 0 | 0 |
| Comparator A* (isododecane based marketed eye shadow) | 0 | 1 | 1 | 1 | 1 |

*Comparator A is a commercial long-wear creaseless cream eye shadow comprising high levels of isododecane. It is a hot poured composition, not an emulsion.

Results:

As is shown in Table 2, the inventive composition of Example 1 had better wear and less flaking than the isododecane based Comparator A composition. This test confirms that the composition of Ex. 1 is non-dying as it experienced substantially less flaking that the isododecane based Comparator A.

Tape Test-Measures Adhesion:

The compositions of Ex. 1 and Comparator A were assessed pursuant to ASTM protocol D3359. Generally, the compositions were applied to a substrate and leveled using a drawdown bar (to achieve uniform thickness). The coated substrate was then air-dried for greater than 30 min.

After drying, a crosshatch pattern was made though the substrate. Detached flakes of coating were removed by brushing with a soft brush. Pressure-sensitive tape was applied over the crosshatch cut. The tape was smoothed into place by using a pencil eraser over the area of the incisions. Tape was then removed by pulling it off rapidly back over itself close to an angle of 180°.

Adhesion of the test compositions to the substrate was assessed on a 0 to 5 scale, 0 being very low adhesion and 5 being high adhesion.

The results of the tape test are shown in Table 3 below.

TABLE 3

| Tape Test | |
|---|---|
| Composition | Rating |
| Ex 1 | 2B |
| Comparator A (isododecane based marketed eye shadow) | 0B |

As is shown about in Table 3, the water-based cream eye shadow composition of Ex 1 had stronger adhesion to the substrate than the isododecane based composition of Comparator A. This result indicates the water-based compositions of the invention have better wear than compositions including volatile organic solvents such as isodoecane.

External Aggression Tests: Assessment of Wear Properties

RubTest Protocol: A 0.1 g of test composition was rubbed onto forearm skin and let dry (~1 min). Thereafter, the skin where the product was applied was rubbed with index finger 20 times.

The area of the skin was graded with naked eye to assess how much product was left on the skin.

The scale uses was: 0 to 3, 0 being no product remaining on the skin and 3 being all product remaining on the skin.

Warm Water Test Protocol:

After the rub test, warm water (>35° C.) was run for 30 seconds down the spots where the test compositions were applied. The running water was allowed to run down the spot and did not hit the composition directly.

How much of each product remained on the skin was then assessed with the naked eye on a 0 to 3 scale, 0 being no product remaining and 3 being all product remaining.

The results of the rub and warm water test are provided below in Table 4

TABLE 4

| Rub/Warm Water Tests | | |
|---|---|---|
| Composition | Rub test rating | Warm water test rating |
| Ex 1 | 2 | 2 |
| Comparator B* (isododecane based marketed eye shadow) | 2 | 1 |

*Comparator B is an isododecane based commercial eye shadow that does not include a sucrose fatty acid ester. This eye shadow is not an emulsion.

As shown in Table 4, the inventive composition of Ex 1 containing a sucrose fatty acid ester are less likely to rub off after water immersion (that is, they are more water-resistant) than the comparator eye shadow, which does not include a sucrose fatty acid ester.

Additional Wear Tests

Water/Sebum Resistance

Contact angle measurements were done on an Attension Tensiometer by Biolin Scientific. The contact angle, θ, is a quantitative measure of wetting of a solid by a liquid. It is defined geometrically as the angle formed by a liquid at the three-phase boundary where a liquid, gas and solid intersect.

A droplet was placed on the glass surface with the testing product drawn down to a uniform thickness and the image of the drop was recorded.

Static contact angle was then defined by fitting Young-Laplace equation around the droplet.

A low contact angle value indicated that the liquid (water or sebum in this case) spread on the surface while a high contact angle value shows poor spreading, meaning water or sebum resistance.

The results of this test are report below in Table 5.

Crease Resistance Assessment

An evaluator applied a test sample to the eye lid area and wore the product for 6 hours. The creasing of the product was then evaluated with naked eye. The results of this test are also reported in Table 5 below.

TABLE 5

| Wear Properties | | | |
|---|---|---|---|
| Composition | Contact angle of water θ [°] at t = 10 sec | Contact angle of sebum θ [°] at t = 10 sec | Creasing |
| Composition According to Invention (pearl at 10%, different from pearl used in Ex 1 or 2) | 60.9 | 13.76 | less |
| Composition omitting thickener ammonium acroyldimethyltaurate/ steareth-25 methacrylate crosspolymer | 58.1 | 15.72 | more |
| composition omitting glyceryl stearate (emulsifier) | 42.2 | 15.76 | less |
| Composition omitting stearic acid | 51.3 | 14.55 | more |

As is shown in Table 5 above, the results of the water/sebum resistance indicate that use of surfactants, stearic acid and glyceryl stearate, improves water resistance, which contributes to the wear and crease-resistance of the compositions of the invention. In addition, the combination of the methacrylate copolymer and glyceryl stearate contributes to sebum resistance which reflects improved wear and crease-resistance.

The results of the creasing assessment show that stearic acid (anionic surfactant) and methacrylate copolymer (thickener) contribute to crease-resistance property as well as water resistance which are important characteristics for a long wear product.

What is claimed is:

1. A cosmetic composition comprising:
   (a) an emulsifying system comprising (i) at least one lipophilic emulsifying surfactant and (ii) at least one sucrose fatty acid ester;
   (b) less than about 5% of at least one film forming polymer selected from an ethylene/acrylic acid copolymer, styrene/acrylates copolymer, and mixtures thereof;
   (c) at least one viscosity increasing agent;
   (d) at least one silicone oil;
   (e) at least one powder, filler, or a mixture thereof;
   (f) water;
   (g) less than about 3% of at least one wax;
   (h) at least one colorant; and
   (i) at least one slip agent;
   said composition being free of volatile organic solvents.

2. The composition of claim 1 in the form of an oil-in-water emulsion.

3. The composition of claim 2 having a viscosity equal to or greater than 20 Pa*s.

4. The composition of claim 3 having a pH from about 5 to about 6.

5. The composition of claim 4 having a density from 0.7 g/cm$^3$ to about 1.5 g/cm$^3$.

6. The composition of claim 5 wherein the emulsifying system (a) is present in an amount from about 0.7% to about 7%, by weight, relative to the weight of the composition.

7. The composition of claim 6 wherein the lipophilic emulsifying surfactant (a)(i) is present in an amount from about 0.2% to about 3%, by weight, relative to the weight of the composition.

8. The composition of claim 7 wherein the sucrose fatty acid ester (a) is present in an amount from about 0.5% to about 5%, by weight, relative to the weight of the composition.

9. The composition of claim 8 wherein the film forming polymer (b) is present in an amount from about 0.5% to about %, by weight, relative to the weight of the composition.

10. The composition of claim 9 wherein the viscosity increasing agent (c) is present in an amount from about 0.1% to about 5%, by weight, relative to the weight of the composition.

11. The composition of claim 10 wherein the at least one silicone oil (d) is present in an amount from about 2% to about 15%, by weight, relative to the weight of the composition.

12. The composition of claim 11 wherein the at least one powder (e) is present in an amount from about 1% to about 15%, by weight, relative to the weight of the composition.

13. The composition of claim 12 wherein water is present in an amount about 20% to about 70%, by weight, relative to the weight of the composition.

14. The composition of claim 13 wherein the at least one colorant (h) is present in an amount from about 0.5% to about 20%, by weight, relative to the weight of the composition.

15. The composition of claim 1 further comprising at least one surfactant in an amount from about 0.1% to about 10%, by weight, relative to the weight of the composition.

16. The composition of claim 15 comprising a slip agent (i) in an amount from about 0.5% to about 20%, by weight, relative to the weight of the composition.

17. The composition of claim 6 wherein the silicone oil (d) is selected from dimethicone, pentaerythrityl tetraethylhexanoate, cyclohexasiloxane, PEG-10 dimethicone, and mixtures thereof.

18. The composition of claim 17 wherein the lipophilic emulsifying surfactant (a)(i) is selected from glyceryl stearate, glycerol stearate citrate, glyceryl ricinoleate, polyethylene glycol stearate, and mixtures thereof.

19. The composition of claim 18 wherein the sucrose fatty acid ester (a)(ii) is selected from sucrose stearate, sucrose distearate, sucrose tristearate, and mixtures thereof.

20. The composition of claim 19 wherein the viscosity increasing agent (c) is selected from ammonium acryloydimethyltaurate/stereath-25 methacrylate crosspolymer, sodium polyacrylate, and mixtures thereof.

21. The composition of claim 20 wherein the film forming polymer (b) is selected from ethylene/acrylic acid copolymer (and) styrene/acrylates copolymer, olefin/acrylate grafted polymer, acrylates copolymer, olefin/acrylic graft emulsion, and mixtures thereof.

22. A cosmetic composition comprising:
(a) from about 0.7% to about 7%, by weight, of an emulsifying system comprising (i) from about 0.2% to about 3%, by weight, of at least one lipophilic emulsifying surfactant selected from glyceryl stearate, and (ii) from about 0.5% to about 4%, by weight, of one at least one sucrose fatty acid ester elected from sucrose tristearate;
(b) from about 0.5% to less than about 5%, by weight, of at least one film forming polymer selected from an ethylene/acrylic acid copolymer, styrene/acrylates copolymer, and mixtures thereof;
(c) from about 0.1% to about 5%, by weight, of at least one viscosity increasing agent selected from ammonium acryloydimethyltaurate/steraeth-25 methacrylate crosspolymer, sodium polyacrylate, and mixtures thereof;
(d) from about 2% to about 15%, by weight, of at least one silicone oil selected from dimethicone, PEG-10 dimethicone, pentaerythrityl tetraethylhexanoate, cyclohexasiloxane, and mixtures thereof;
(e) from about 1% to about 15%, by weight, of at least one powder selected from dipehnyl dimethicone/vinyl diphenyl dimethicone/silsesquioxane crosspolymer, vinyl dimethicone/methicone silsesquioxane crosspolymer, acrylonitrile/methyl methacrylate/vinylidene chloride copolymer, and mixtures thereof and mixtures thereof;
(f) from about 20% to about 70%, by weight, of water;
(g) less than about 3%, by weight, of at least one wax;
(h) from about 0.5% to about 20%, by weight, of at least one colorant;
(i) from about 0.1% to about 10%, by weight, of at least one surfactant selected from stearic acid, sorbitan sesquioleate, sorbitan sesquioleate, and mixtures thereof; and
(j) from about 0.5% to about 20%, by weight, of at least one slip agent selected from dimethicone/vinyl dimethicone crosspolymers and glycerin;
said composition being free of volatile organic solvents and said composition being in the form of an eye shadow; all weights being relative to the total weight of the composition.

23. A method of improving at least one property chosen from long wear, comfort, crease-resistance, and ease of removal, of an eye shadow cosmetic composition, said method comprising including the cosmetic composition:
(a) an emulsifying system comprising (i) at least one lipophilic emulsifying surfactant, and (ii) at least one sucrose fatty acid ester;
(b) less than about 5% of at least one film forming polymer selected from an ethylene/acrylic acid copolymer, styrene/acrylates copolymer, and mixtures thereof;
(c) at least one viscosity increasing agent;
(d) at least one silicone oil;
(e) at least one powder, filler, or a mixture thereof;
(f) water; and
(g) less than about 3% of at least one wax.

24. A method of making up the eyes complying applying to the skin around the eyes a composition according to claim 1.

25. A process of making the cosmetic composition of claim 1 comprising:
(a) providing an emulsifying system comprising (i) at least one lipophilic emulsifying surfactant, and (ii) at one at least one sucrose fatty acid ester;

(b) providing at least one film forming polymer selected from an ethylene/acrylic acid copolymer, styrene/acrylates copolymer, and mixtures thereof;
(c) providing at least one viscosity increasing agent;
(d) providing at least one silicone oil
(e) providing at least one powder, filler, or a mixture thereof;
(f) providing water
(g) providing at least one wax;
(h) providing at least one colorant;
(i) providing at least one slip agent; and
(j) combining the above components such as to provide a uniform, blended composition.

26. The composition of claim 1, in the form of an eye shadow.

* * * * *

UNITED STATES PATENT AND TRADEMARK OFFICE
CERTIFICATE OF CORRECTION

PATENT NO. : 9,526,678 B2
APPLICATION NO. : 14/565985
DATED : December 27, 2016
INVENTOR(S) : Heather Yoonsoo Lee et al.

Page 1 of 1

It is certified that error appears in the above-identified patent and that said Letters Patent is hereby corrected as shown below:

Column 21, Line 1, "The composition of claim 1" should read --The composition of claim 1,--;
　　Line 3, "The composition of claim 2" should read --The composition of claim 2,--;
　　Line 7, "The composition of claim 4" should read --The composition of claim 4,--;
　　Line 12, "The composition of claim 6" should read --The composition of claim 6,--:
　　Line 17, "acid ester (a)" should read --acid ester (a)(ii)--;
　　Line 20, "The composition of claim 8" should read --The composition of claim 8,--;
　　Line 28, "The composition of claim 10" should read --The composition of claim 10,--;
　　Line 35, "The composition of claim 12" should read --The composition of claim 12,--;
　　Line 42, "The composition of claim 1" should read --The composition of claim 1,--;
　　Line 48, "The composition of claim 6" should read --The composition of claim 6,--;
　　Line 56, "The composition of claim 18" should read --The composition of claim 18,--;
　　Line 63, "The composition of claim 20" should read --The composition of claim 20,--.

Column 22, Line 28, "nylidene chloride copolymer, and mixtures thereof and mixtures thereof:" should read --nylidene chloride copolymer, and mixtures thereof;--;
　　Line 64, "claim 1 comprising:" should read --claim 1, comprising:--.

Signed and Sealed this
Twenty-fourth Day of July, 2018

Andrei Iancu
*Director of the United States Patent and Trademark Office*